United States Patent
Steiner et al.

(10) Patent No.: US 9,308,065 B2
(45) Date of Patent: Apr. 12, 2016

(54) TOOTH CLEANING MECHANISM

(71) Applicants: Mark W. Steiner, Slingerlands, NY (US); Aren Y. Paster, Ballston Spa, NY (US); Daniel F. Walczyk, Brunswick, NY (US)

(72) Inventors: Mark W. Steiner, Slingerlands, NY (US); Aren Y. Paster, Ballston Spa, NY (US); Daniel F. Walczyk, Brunswick, NY (US)

( * ) Notice: Subject to any disclaimer, the term of this patent is extended or adjusted under 35 U.S.C. 154(b) by 51 days.

(21) Appl. No.: 13/999,914

(22) Filed: Apr. 2, 2014

(65) Prior Publication Data

US 2015/0282911 A1 Oct. 8, 2015

(51) Int. Cl.
- *A61C 17/34* (2006.01)
- *A46B 9/04* (2006.01)
- *A61C 17/22* (2006.01)

(52) U.S. Cl.
CPC ............ *A61C 17/3445* (2013.01); *A46B 9/045* (2013.01); *A61C 17/228* (2013.01); *A46B 2200/1066* (2013.01)

(58) Field of Classification Search
CPC .... A61C 17/3445; A61C 17/32; A61C 17/34; A61C 17/228; A46B 9/045; A46B 2200/1066
See application file for complete search history.

(56) References Cited

U.S. PATENT DOCUMENTS

| | | | |
|---|---|---|---|
| 4,382,309 A | 5/1983 | Collis | |
| 4,493,125 A | 1/1985 | Collis | |
| 4,619,009 A | 10/1986 | Rosenstatter | |
| 4,784,294 A | 11/1988 | Dickinson | |
| 6,152,733 A | 11/2000 | Hegemann et al. | |
| 6,223,376 B1 | 5/2001 | Lee | |
| 6,536,066 B2 | 3/2003 | Dickie | |
| 6,892,413 B2 | 5/2005 | Blaustein et al. | |
| 8,584,291 B2 * | 11/2013 | Thompson | 15/22.1 |
| 2009/0276972 A1 | 11/2009 | Dugan | |
| 2011/0072605 A1 | 3/2011 | Steur | |
| 2011/0154595 A1 | 6/2011 | Hill | |
| 2011/0247159 A1 | 10/2011 | Steur et al. | |
| 2011/0289709 A1 | 12/2011 | Attaway | |
| 2015/0250571 A1 * | 9/2015 | Oelgiesser | A61C 17/349 15/22.2 |

OTHER PUBLICATIONS

Galel, "Oral Hygiene Device for Disabled Users," Rensselaer Polytechnic Institute, 2011.
US Provisional Patent Appln. "Oral Hygiene Capstone," Galel et al, filed Feb. 11, 2011; Admitted Prior Art.

* cited by examiner

*Primary Examiner* — Shay Karls

(57) ABSTRACT

A tooth cleaning device for the disabled eliminates the need for the user to rotate her/his wrist while brushing teeth, and provides approximately the same profile as a standard manual toothbrush. The device is capable of effectively brushing all three sides of all upper or lower teeth simultaneously, and utilizes a commercially available battery powered toothbrush power source to provide the power necessary for effective teeth cleaning action. An open top U-shaped track has a number of distinct operatively connected brush bristle mounting heads reciprocal and retained within the track, with a number of bristles extending up from each of the heads. A device, such as an opening in a central head, a linkage, and a battery powered oscillating shaft, provide back and forth arcuate reciprocal movement of the heads within the track to provide tooth cleaning by the bristles.

20 Claims, 7 Drawing Sheets

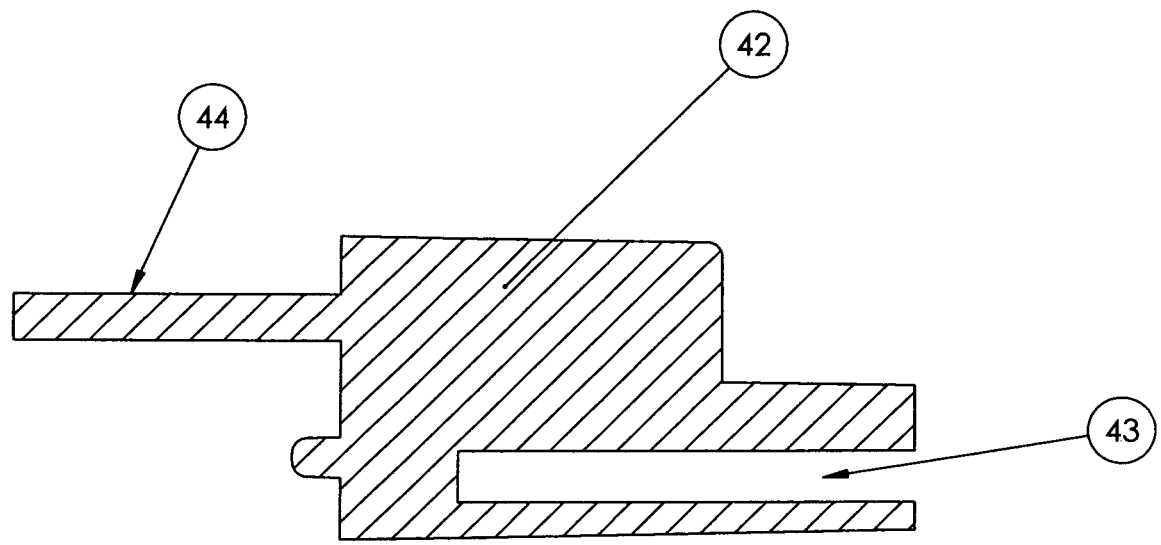
FIGURE 6
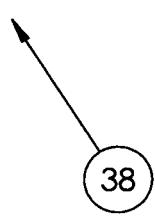

TOOTH CLEANING MECHANISM

CROSS-REFERENCE TO RELATED APPLICATION

This application is based upon U.S. Provisional Application Ser. No. 61/811,349 filed Apr. 12, 2013, the disclosure of which is incorporated by reference herein.

BACKGROUND AND SUMMARY OF THE INVENTION

Maintaining proper dental hygiene is an important part of maintaining overall health. For people with permanent or temporary disabilities the task of brushing teeth can be between challenging or impossible without assistance. There have been many proposals for dealing with this problem, most with various drawbacks or difficulties either in production or use.

One prior art proposal by Galel et al, the subject of a U.S. provisional patent application filed Feb. 11, 2011 and an article published by Rensselaer Polytechnic Instituted in 2011 entitled "Oral Hygiene for Disabled Users," utilizes a U-shaped base with a raised track and with raised bristle elements movable on the track. The bristle elements are arcuately reciprocated on the track with a battery powered rotating shaft connected by an output gear to a slotted projection on the bristle elements. While the Galel et al device has a number of desirable features, the manner of use requires the user to bite down on the base and the profile of the entire device is high, both undesirable features. Also the output gear adds undesirable complexity.

Another device, disclosed in the Dugan U.S. Published Patent Application 2009/0276972, has a lower profile than the Galel et al device. Dugan utilizes a U-shaped insert with three sets of bristles in a U-shaped base and effects cleaning by vibrating the insert using a specially designed vibrator. Vibration within a user's mouth may provide an uncomfortable feeling to some individuals, and the vibratory action may not provide an optimum cleaning action.

A number of other proposals dealing with the same problem as the invention, namely facilitating teeth cleaning for a disabled person or baby, such as in U.S. Pat. Nos. 6,223,376 and 6,152,733, and U.S. Published Patent Applications 2011/0072605, 2011/0154595, 2011/0247159, and 2011/0289709, have been provided. Each has one or more drawbacks that are believed to be overcome by the present invention.

The invention provides a device with a low profile and optimum teeth cleaning action. The device of the invention eliminates the need for the user to rotate her or his wrist while brushing teeth thereby facilitating use by disabled people, and provides substantially the same profile as a standard manual toothbrush. The device is capable of effectively brushing all three sides of each tooth (the front, back, and top or bottom) simultaneously. The novel components of the invention are relatively easy to manufacture and the invention preferably utilizes a conventional, readily commercially available, battery powered toothbrush power source to provide the power necessary for the teeth cleaning action.

According to one aspect of the invention there is provided a tooth cleaning assembly comprising: A substantially open top substantially U-shaped track dimensioned to fit within a human being's mouth containing teeth. [The term "top" is used just to provide a basis for description of the track and does not imply that the open portion of the track is always vertically above the rest of the track. In fact, when the device is used to clean bottom teeth, the open part of the track will be the bottom.] At least one, and preferably a plurality, of distinct brush bristle mounting heads, mounted to be reciprocal within the track, retained within the track, and operatively connected together. A plurality of tooth-engagable bristles (that is bristles generally like those on a conventional toothbrush) operatively connected to each of the heads and extending therefrom to engage a human being's teeth when positioned within a human being's mouth. And, a device facilitating back and forth reciprocal movement of the heads within the track to provide tooth cleaning by the bristles.

The bristles may include first and second distinct rows of bristles extending past the track away therefrom. In one embodiment, such as provided per se in U.S. Pat. Nos. 4,382,309 and 4,493,125 (the disclosures of which are incorporated by reference herein), the bristles of the first and second rows are curved inwardly, toward each other, at portions thereof past the track. There also may be provided a third row of bristles, shorter than the bristles of the first and second rows, extending substantially straight away from the heads and between the first and second rows of bristles.

The heads are operatively connected together by connections that allow some relative pivotal movement of the heads with respect to each other in order to accommodate arcuate reciprocating action. For example the connections may comprise tongue and groove connectors which allow the relative pivotal movement of the heads with respect to each other. The plurality of heads may include a central head, and the central head preferably includes a manifestation, preferably either in the form of an opening or a projection, most desirably an opening, which comprises the device for facilitating back and forth reciprocal movement of the heads.

In addition to providing a manifestation on or in one of the heads, the device which facilitates back and forth arcuate reciprocal movement of the heads within the track may further comprise a linkage which can operatively connect a powered shaft oscillating in a dimension parallel to the dimension of reciprocation of the heads to the manifestation to effect reciprocating movement of the heads. The assembly according to the invention is also preferably provided in combination with a conventional battery powered toothbrush power source having a powered shaft oscillating in a dimension parallel to the dimension of reciprocation of the heads, the powered shaft connected to the linkage; and preferably the manifestation comprises an opening in one of the heads, the opening receiving a portion of the linkage therein.

According to another aspect of the invention there is provided a tooth cleaning assembly comprising: A substantially U-shaped track having an open top (again the use of the word "top" being for descriptive purposes and not implying that the open portion is always the vertically highest portion of the track). A plurality of distinct brush bristle mounting heads reciprocal within the track, retained substantially completely within the track, and operatively connected together. And, a plurality of tooth-engagable bristles operatively connected to each of the heads and extending upwardly from the open top of the track and the heads to engage a human being's teeth when positioned within a human being's mouth to effect cleaning of the front, back, and top or bottom of the human's teeth by reciprocally moving within the track with the heads.

The bristles may include first and second distinct rows of bristles extending upwardly from the track that are curved inwardly, toward each other, (as in U.S. Pat. Nos. 4,382,309 and 4,493,125) at portions thereof past the track to engage the fronts and backs of teeth that they come into contact with. A third row of bristles, shorter than the bristles of the first and second rows, may be provided extending substantially straight away from the heads and between the first and second rows of bristles to engage the tops or bottoms of teeth that they come into contact with.

As according to the previous aspect of the invention, the heads are preferably operatively connected together by connectors which allow relative pivotal movement of the heads with respect to each other as they arcuately reciprocate within the track. Desirably, the heads are retained within the track by an inward taper of the open top of the track and a cooperating shape of the heads. The track may be made of relatively flexible material, such as nylon, so that the heads may be snap fit into the track through the open top thereof, or the heads and track may be designed so that the heads may be slid into the track at open ends of the top of the "U."

According to yet another aspect of the invention a tooth cleaning assembly is provided comprising: A substantially U-shaped track having an open top and a central open area at the bottom curve of the "U." A plurality of distinct brush bristle mounting heads reciprocal within the track, and operatively connected together, and one of the heads having a manifestation therein or thereon aligned with the central open area of the track for cooperation with a shaft which can oscillate in a plane parallel to the dimension of reciprocation of the heads. A plurality of tooth-engagable bristles operatively connected to each of the heads and extending upwardly from the open top of the track. And a guide channel extending outwardly from the track and operatively connected thereto for supporting and guiding an oscillating shaft.

The assembly is preferably provided in combination with a linkage extending through the guide channel and engaging the manifestation; and also in combination with a hand-held powered device having an oscillating shaft extending outwardly therefrom and engaging the linkage to effect powered reciprocation of the heads. The hand-held powered device preferably comprises a conventional battery powered toothbrush power source, such as the commercially available Braun ORAL-B® toothbrush power source, or the power sources as shown in U.S. Pat. No. 6,536,066 or 6,892,413 (the disclosures of which are incorporated by reference herein, including the prior art in the '413 patent).

The track and guide channel preferably comprise a unitary piece of biocompatible plastic (e.g. injection molded of nylon, polypropylene, or another readily available plastic). Also, a permanently affixed, or removable, cover (also of plastic) may be provided for covering the guide channel.

It is the primary object of the present invention to provide an assembly that may readily be used by permanently or temporarily disabled or injured people to effectively clean their teeth without assistance from others. This and other objects of the invention will become from the detailed description of the drawings, and from the appended claims.

BRIEF DESCRIPTION OF THE DRAWINGS

FIG. 6 is a side cross-sectional view of the exemplary linkage of the assembly of FIG. 1;

DETAILED DESCRIPTION OF THE DRAWINGS

Figure 1:
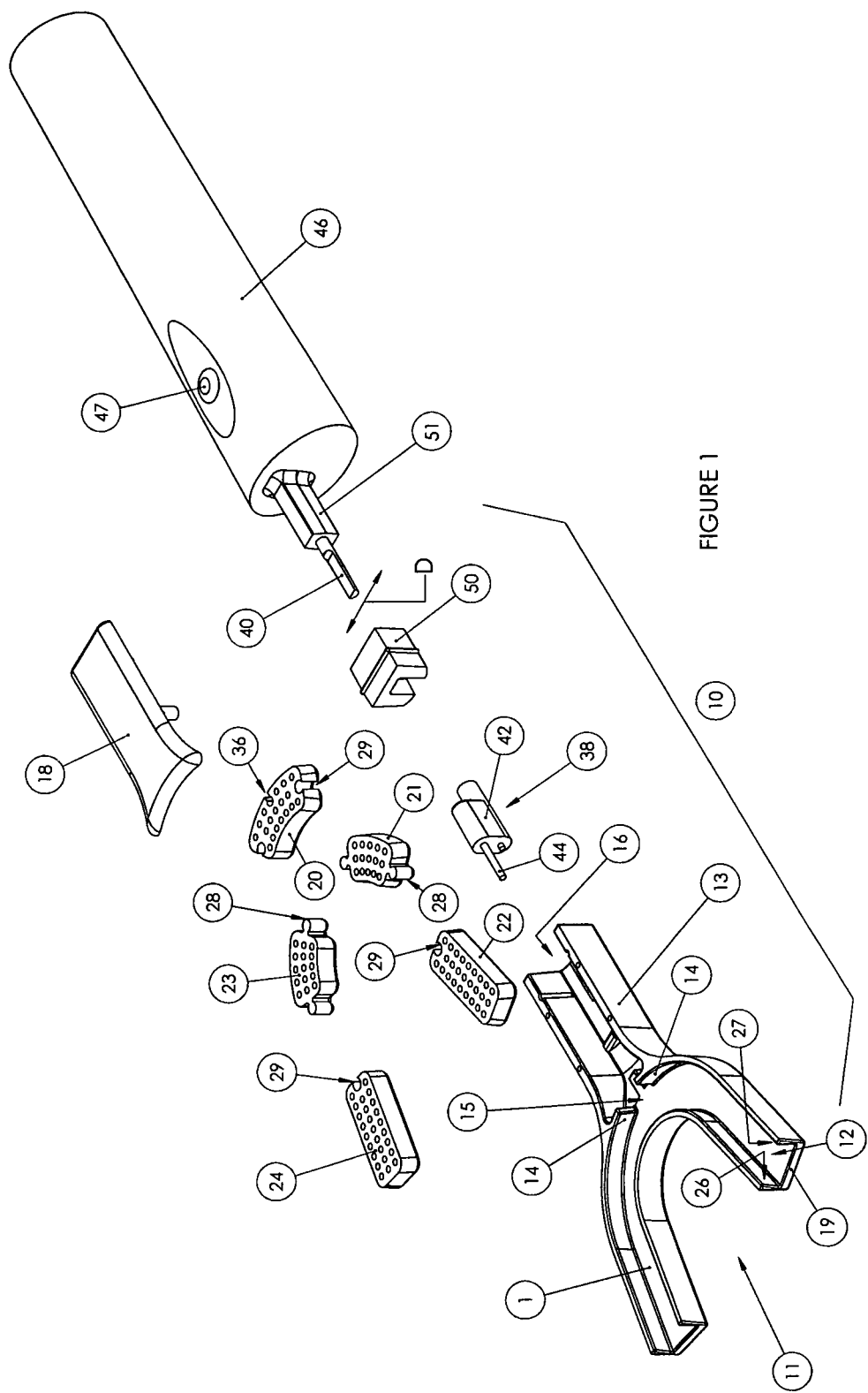
FIG. 1 is a top perspective exploded view of an exemplary embodiment of a tooth cleaning assembly according to the present invention, in combination with a commercially available battery powered toothbrush power source.
Figure 2:
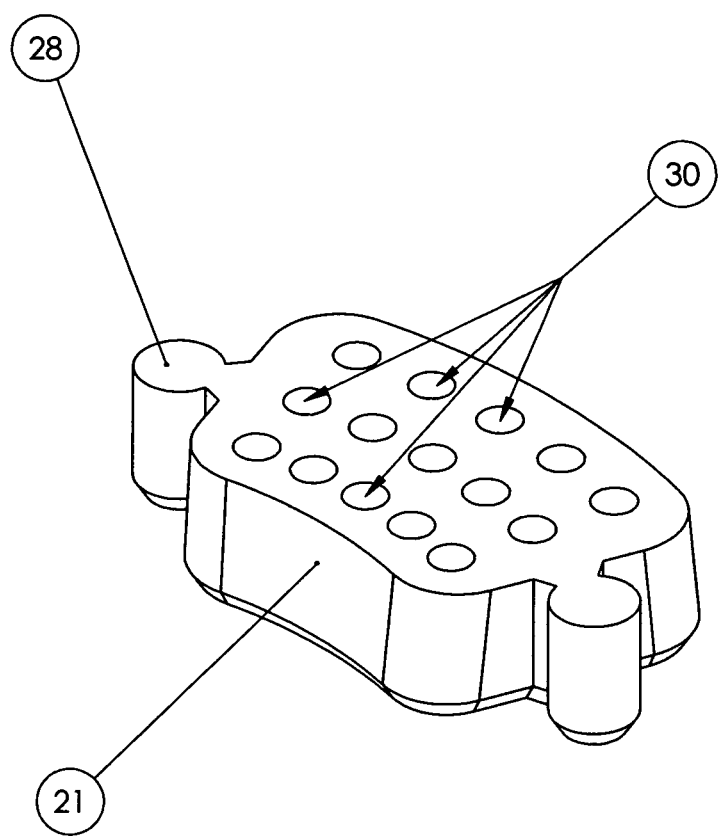
FIG. 2 is a top perspective view of one of the brush bristle mounting heads, per se, of the assembly of FIG. 1.

FIG. 1 illustrates a top perspective exploded view of one exemplary embodiment of a tooth cleaning assembly 10 according to the invention. One of the major novel components comprises a substantially U-shaped track, shown generally by reference numeral 11, having a substantially open top 12. The term "top" as used in the present specification and claims is merely for the purposes of facilitating description of the various components of the invention and is not suggested that the open area 12 will always be vertically above other elements of the track 11. In fact, in use, normally the open area 12 will be disposed in a generally horizontal plane and will either provide the top or bottom of the track 11 depending upon whether the assembly 10 is used to clean the top or bottom teeth, respectively, of a human user's mouth.

In the preferred embodiment illustrated in FIG. 1, the track 11 is operatively connected to a guide channel 13 extending outwardly therefrom, at the bottom 14 of the "U," and an opening 15 in provided in the bottom of the "U" provided between the track 11 and the channel 13. In one desirable embodiment the track 11 and channel 13 comprise a unitary piece of biocompatible plastic, e. g. injection molded nylon or other common biocompatible plastic. Desirably, although not essential, the plastic comprising the track 11 is low friction, such as nylon, or is coated with a low friction material, such as polytetraflouroethylene.

Figure 7:
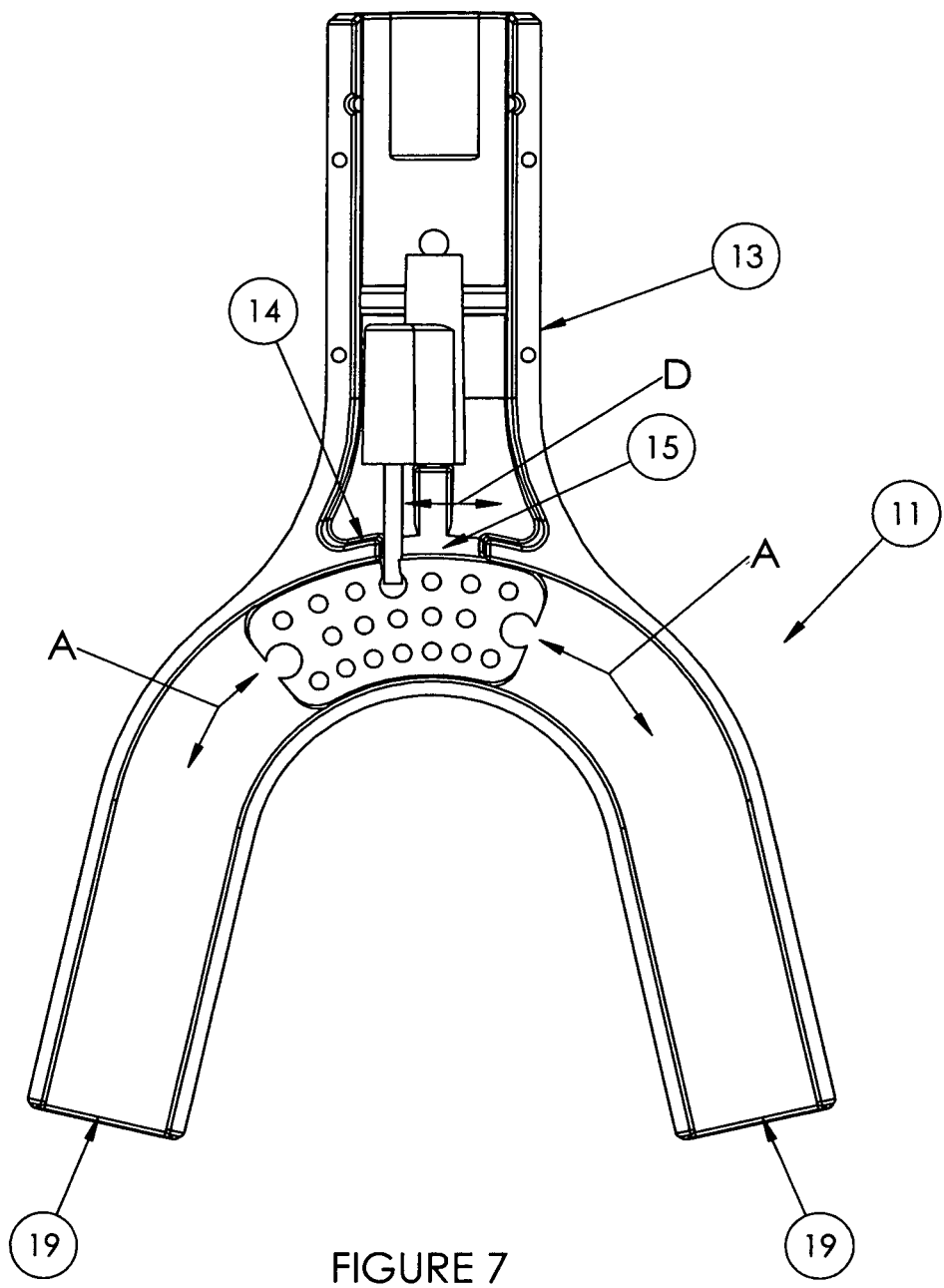
FIG. 7 is a top schematic view of the assembly of FIG. 1, with the cover for the channel removed for clarity of illustration, showing just the central head of the assembly at one end of the range of its arcuate reciprocating travel.
Figure 8:
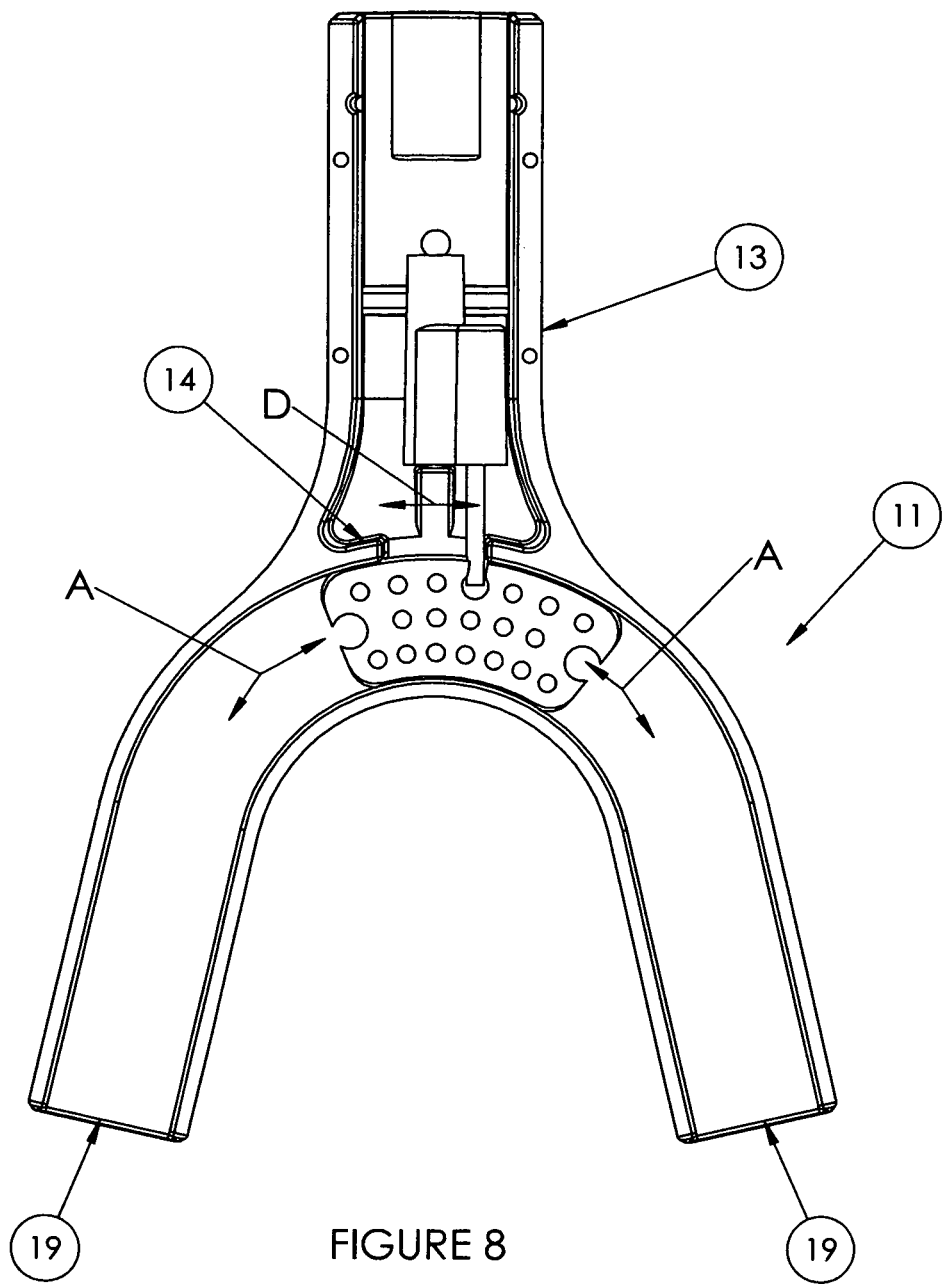
FIG. 8 is a view like that of FIG. 7 schematically showing the central head of FIG. 7 at the opposite end of the range of its reciprocating travel.

The free ends 19 of the "U" are preferably open, as illustrated in FIGS. 1, 7 and 8, but may be closed.

The guide channel 13 preferably also has an open top 16 which, after assembly of the components, is covered by a top cover 18. The top cover 18 may also be a piece of plastic and may be removable, connected to the channel 13 by any suitable conventional structure (such as clips, an elastic band, removable adhesive, etc.) allowing disconnect thereof, or may be affixed with permanent adhesive, ultrasonic welding, a press fit, or otherwise substantially permanently affixed to the guide channel 13, to cover the open top 16 thereof.

The assembly 10 also includes at least one brush bristle mounting head 20 arcuately reciprocal (as indicated schematically by the arrows A in FIGS. 7 & 8) within the track 11. Preferably, a plurality of heads are provided, such as the heads 20, 21, 22, 23 and 24. The heads 20-24 are retained within the track 11 so that regardless of the orientation of the track 11 the heads will not fall out through the open top 12 thereof. This may be easily accomplished by providing an inward taper of the open top 12 of the track 11, as shown schematically at 26 and 27 in FIG. 1, and by providing a cooperating configuration of the heads 20-24.

The heads 20-24 are preferably made of a biocompatible plastic, most desirably a low friction plastic such as nylon. The heads 20-24 may be injection molded or otherwise produced by conventional techniques.

The track 11 may be made of relatively flexible material so that the heads 20-24 may be snap fit into said track 11 through the open top 12 thereof. Alternatively, depending upon the configuration of the heads 20-24, they may be slid into open free ends 19 of the track 11. While five heads 20-24 (the end heads 22, 24 being substantially the same in the embodiment illustrated, and the heads 21 and 23 being mirror images of each other, while the central head 20 is unique) are illustrated in the drawings, it is to be understood that that is merely exemplary and any number of heads may be provided.

The heads 20-24 are operatively connected together to allow relative pivotal movement therebetween as they arcuately reciprocate (see FIGS. 7 & 8) in the track 11. While any number of conventional mechanisms may be utilized for this purpose in the preferred embodiment illustrated in the drawings the operative pivotal connections are provided by tongue 28 and groove 29 connectors, preferably shaped as illustrated in FIGS. 1-5. That is the tongues 28 have a substantially continuously curved operable exterior, and the grooves 29 a cooperating curved configuration. Tongues 28 and grooves 29 may be positioned on any of the heads 20-24 as long as they functionally cooperate, not just in the manner illustrated.

Each of the heads 20-24 preferably includes a plurality of bristle mounting openings 30 in the top surface thereof (the surface corresponding to the open top 12 of the track 11). As illustrated in FIGS. 1-5 it is desirable to provide three substantially parallel rows of openings 30 in at least some of, and preferably in each of, the heads 20-24. A plurality of conventional (e. g. nylon) toothbrush bristles, shown schematically at 31-33 in FIG. 3 (the bristles are not shown in the other FIGURES only for clarity of illustration but are preferably provided in each opening 30), are mounted in each opening 30. The mounting of the bristles 31-33 within the openings 30 may be accomplished by any suitable mechanism, such as utilized in conventional manual toothbrushes.

Figure 3:
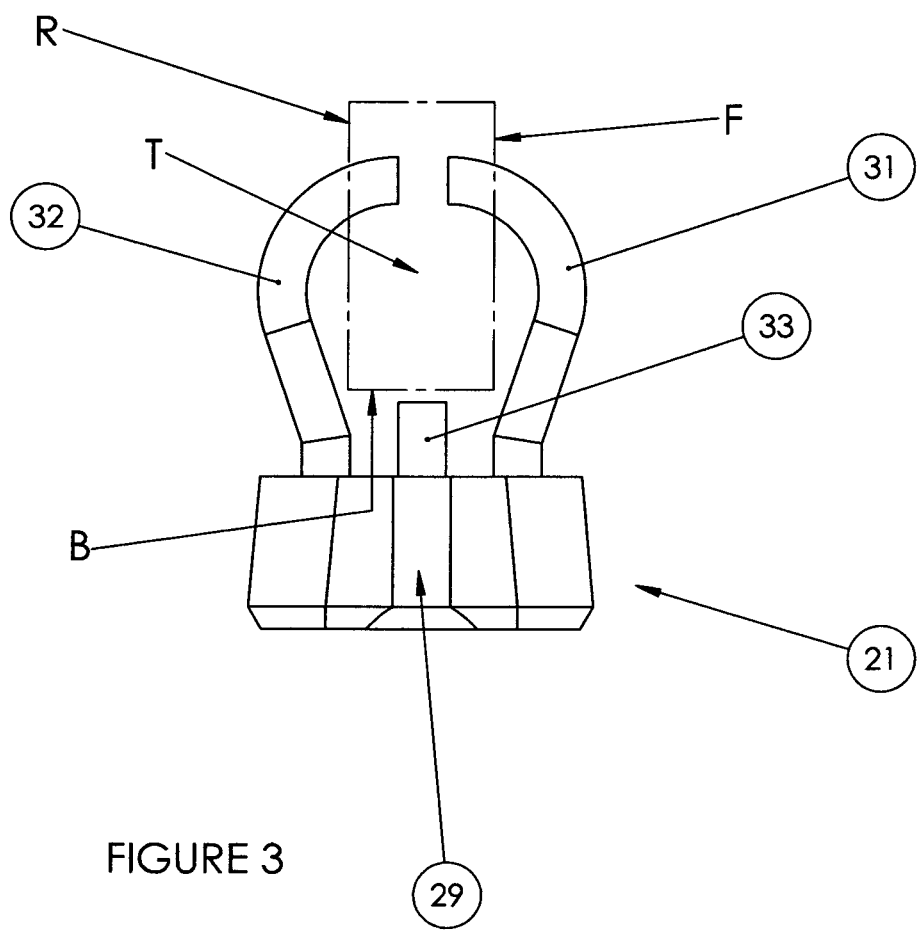
FIG. 3 is an end schematic view of the head of FIG. 2 showing exemplary bristles mounted in the head with a tooth shown in dotted line.
Figure 4:
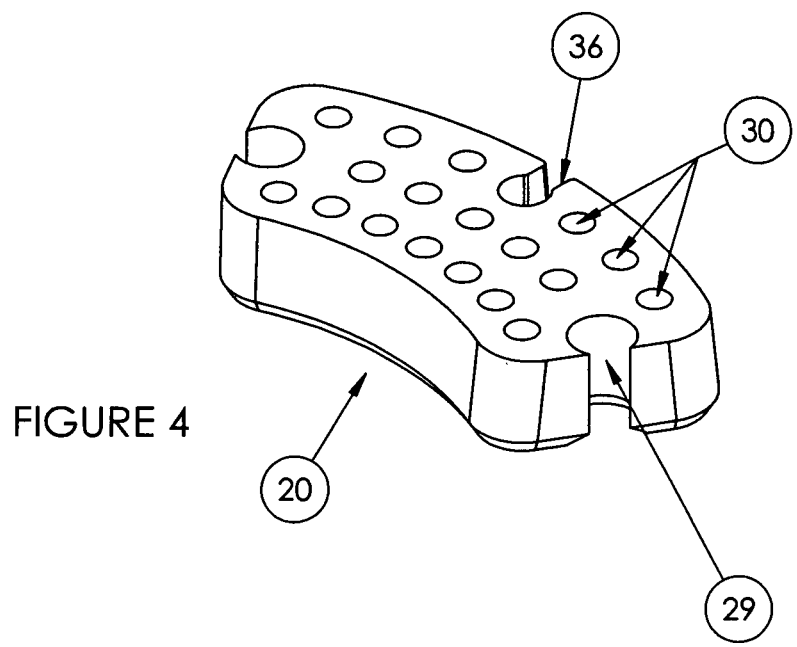
FIG. 4 is top perspective view of the central head of the assembly of FIG. 1.
Figure 5:
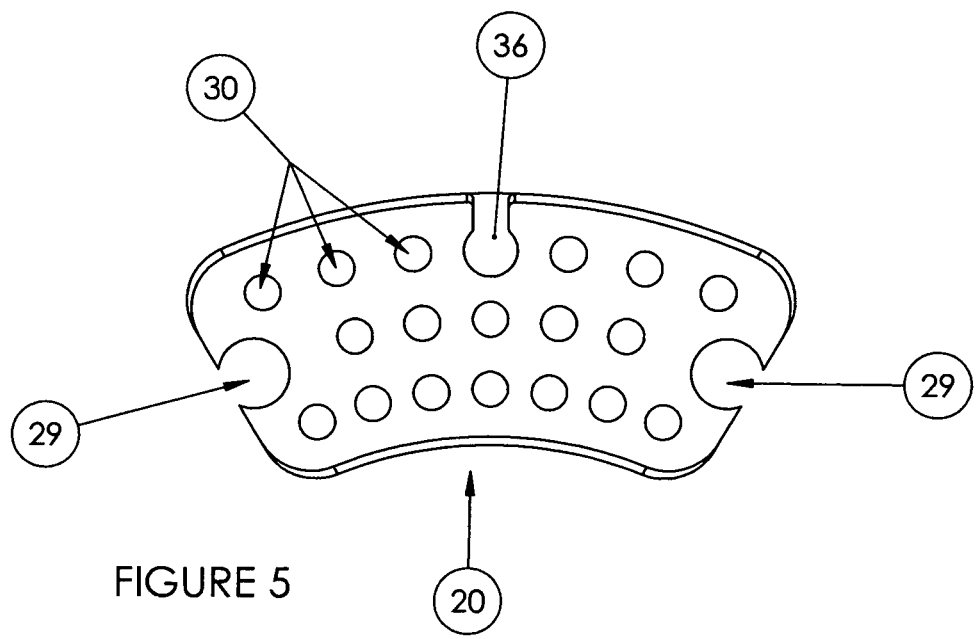
FIG. 5 is a top view of the central head of FIG. 4.

While the bristles 31-32 may have a wide variety of configurations, preferably they take the form of a COLLIS CURVE®, such as shown in U.S. Pat. Nos. 4,382,309 and 4,493,125, which have been incorporated by reference herein. That is, the bristles include first and second distinct rows of bristles, 31, 32, respectively, extending past the track 11 through the open top 12 thereof and away therefrom. As seen in FIG. 3, the bristles 31, 32 of the first and second rows are curved inwardly, toward each other, at portions thereof past ("above") the open top 12 of the track 11. In use the inwardly curved top ends of the bristles 31, 32 will engage the front F and rear R faces of a human's tooth, shown in dotted line at T in FIG. 3.

The plurality of bristles also preferably comprises a third row of bristles 33, shorter than the bristles 31, 32, of the first and second rows. Bristles 33 extend substantially straight away from the head (e. g. head 21 in FIG. 3) in which they are mounted, and are between the first and second rows of bristles 31, 32. The bristles 33 will engage the top or bottom, depending upon which set of teeth are being worked upon, B (FIG. 3) of a tooth T in a human user's mouth.

The assembly 10 also includes a device which facilitates back and forth reciprocal movement of the heads 20-24 within the track 11 to provide tooth cleaning by the bristles 31-33. The device preferably comprises a manifestation 36 (see FIGS. 1, 4, 5, 7 & 8) on or in one of the heads, typically the central head 20 as seen most clearly in FIGS. 4 & 5. The manifestation 36 is illustrated in the drawings as an opening in a central portion of central head 20, but alternatively it could comprise a projection, collar, or other type of manifestation as long as it accomplishes its desired purpose.

The device which facilitates back and forth reciprocal movement of the heads 20-24 within the track 11, in addition to the manifestation 36, preferably further comprises a linkage 38 (see FIGS. 1 & 6) which can operatively connect a powered shaft (40 in FIG. 1) oscillating in a dimension D (FIGS. 1, 7 & 8) generally parallel to the dimension of reciprocation of the heads 20-24 to effect reciprocating movement thereof. In the embodiment illustrated in the drawings, the linkage 38 comprises a body 42 having an opening 43 (FIG. 6) at the bottom thereof which is parallel to the shaft 40 and dimensioned to receive the shaft 40 (e. g. by a press fit or interference fit), and a shaft 44 extending outwardly from the top of the body 42 substantially parallel to the opening 43 and away from the shaft 40.

The shaft 44 extends into the opening 36 and the oscillation of the shaft 40 translates into oscillation of the shaft 44 in dimension D, which in turn effects reciprocation of the heads 20-24 in the track 11 as indicated by arrows A-A, as further indicated schematically at the opposite ends of travel of the central head 20 in FIGS. 7 & 8.

The assembly 10 preferably is provided in combination with a conventional battery powered toothbrush power source 46 (FIG. 1) having a powered shaft 40 oscillating in the dimension D, the powered shaft 40 connected to the linkage 38. The source 46 may be the commercially available Braun ORAL-B® power source having an on-off switch 47, or the power sources such as shown in U.S. Pat. Nos. 6,536,066 and 6,892,413, which have been incorporated by reference herein. The conventional power sources 46 often have a rotating electric motor shaft that, via a cam or some sort of linkage, results in oscillation of the shaft 40 extending outwardly from the source 46.

As also illustrated in FIG. 1, if necessary or desirable a retention insert 50 in channel 13 may be provided to stabilize the shaft 40 when connected to the linkage 38 in channel 13. The retention insert 50 typically engages the shaft 40-surrounding projection 51 of the conventional power source 46.

In a typical procedure for using the assembly 10, the user puts toothpaste, or other tooth cleaning compound, on the bristles 31, 32, and/or 33. If the power source 46 is not already connected, the shaft 40 is inserted into the opening 43 of the linkage 42; or all of the elements 42, 50, 40 are placed in the open top 16 of the channel 13 and the shaft 44 into opening 36, and then the cover 18 placed over the channel 13 open top 16.

To brush her/his upper teeth, the user inserts the track 11 into her/his mouth so that bristles 31-33 are in contact with the fronts F, rears R, and bottoms B of substantially all of the user's top teeth. Then the switch 47 is pressed to turn the power source 46 on. That results in oscillation of the shaft 40 in dimension D, which in turn results in oscillation of the shaft 44. Oscillation of shaft 44 in turn causes back and forth arcuate reciprocation of the heads 20-24 from one end of travel (as in FIG. 7) to the other end of travel (as in FIG. 8), as indicated by arrows A in FIGS. 7 & 8. The bristles 31-33 effectively clean the user's top teeth T during this reciprocation.

To clean her/his bottom teeth the user merely inverts the track 11 before placing it in her/his mouth, and otherwise repeats the steps set forth above.

While the invention has been herein shown and described in a preferred embodiment thereof it is to be understood that many modifications may be made thereof within the scope of the invention, which scope is to be accorded the broadest interpretation of the appended claims to encompass all equivalent structures and devices.

What is claimed is:

1. A tooth cleaning assembly comprising:
    a substantially open top substantially U-shaped track dimensioned to fit within a human being's mouth containing teeth;
    at least one brush bristle mounting head reciprocal within said track and retained within said track;

a plurality of tooth-engagable bristles operatively connected to said at least one head and extending therefrom to engage a human being's teeth when positioned within a human being's mouth; and a device which facilitates back and forth reciprocal movement of said at least one head within said track to provide tooth cleaning by said bristles.

2. An assembly as recited in claim 1 wherein said bristles include first and second distinct rows of bristles extending past said track away therefrom.

3. An assembly as recited in claim 2 wherein said bristles of said first and second rows are curved inwardly, toward each other, at portions thereof past said track.

4. An assembly as recited in claim 3 further comprising a third row of bristles, shorter than the bristles of said first and second rows, extending substantially straight away from said at least one head and between said first and second rows of bristles.

5. An assembly as recited in claim 1 wherein said at least one head comprises a plurality of heads that are operatively connected together by tongue and groove connectors which allow relative pivotal movement of said heads with respect to each other.

6. An assembly as recited in claim 5 wherein said plurality of heads includes a central head, said central head including a manifestation comprising said device for facilitating back and forth reciprocal movement of said heads.

7. An assembly as recited in claim 1 wherein said at least one head comprises a plurality of heads operatively connected together, and wherein said device facilitating back and forth reciprocal movement of said heads within said track comprises a manifestation on or in one of said heads.

8. An assembly as recited in claim 7 wherein said device further comprises a linkage which can operatively connect a powered shaft oscillating in a dimension generally parallel to the dimension of reciprocation of said heads to effect reciprocating movement thereof.

9. An assembly as recited in claim 8 in combination with a conventional battery powered toothbrush power source having a powered shaft oscillating in a dimension generally parallel to the dimension of reciprocation of said heads, said powered shaft connected to said linkage; and wherein said manifestation comprises an opening in one of said heads, said opening receiving a portion of said linkage therein.

10. A tooth cleaning assembly comprising:
a substantially U-shaped track having an open top;
a plurality of distinct brush bristle mounting heads reciprocal within said track, retained substantially completely within said track, and operatively connected together; and
a plurality of tooth-engagable bristles operatively connected to each of said heads and extending upwardly from the open top of said track and said heads to engage a human being's teeth when positioned within a human being's mouth to effect cleaning of the front, back, and top or bottom of the human's teeth by said heads reciprocally moving within said track.

11. An assembly as recited in claim 10 wherein said bristles include first and second distinct rows of bristles extending upwardly from said track that are curved inwardly, toward each other, at portions thereof past said track to engage the fronts and backs of teeth that they come into contact with.

12. An assembly as recited in claim 11 further comprising a third row of bristles, shorter than the bristles of said first and second rows, extending substantially straight away from said heads and between said first and second rows of bristles to engage the tops or bottoms of teeth that they come into contact with.

13. An assembly as recited in claim 10 wherein said heads are operatively connected together by connectors which allow relative pivotal movement of said heads with respect to each other as they reciprocate within said track.

14. An assembly as recited in claim 10 wherein said heads are retained within said track by an inward taper of the open top of said track and a cooperating configuration of said heads.

15. An assembly as recited in claim 14 wherein said track is made of relatively flexible material so that said heads may be snap fit into said track through said open top thereof.

16. A tooth cleaning assembly comprising:
a substantially U-shaped track having an open top and a central open area at the bottom curve of said U;
a plurality of distinct brush bristle mounting heads reciprocal within said track, and operatively connected together;
one of said heads having a manifestation therein or thereon aligned with said central open area of said track for cooperation with a shaft oscillating in a plane parallel to the dimension of reciprocation of said heads;
a plurality of tooth-engagable bristles operatively connected to each of said heads and extending upwardly from the open top of said track; and
a guide channel extending outwardly from said track and operatively connected thereto for supporting and guiding an oscillating shaft.

17. An assembly as recited in claim 16 in combination with a linkage extending through said guide channel and engaging said manifestation; and also in combination with a hand-held powered device having an oscillating shaft extending outwardly therefrom and engaging said linkage to effect powered reciprocation of said heads.

18. An assembly as recited in claim 17 wherein said hand-held powered device comprises a conventional battery powered toothbrush power source.

19. An assembly as recited in claim 16 wherein said track and guide channel comprise a unitary piece of biocompatible plastic.

20. An assembly as recited in claim 19 wherein said track and heads are made of a low friction biocompatible plastic.

* * * * *